United States Patent [19]

Mericle

[11] Patent Number: 5,752,964
[45] Date of Patent: May 19, 1998

[54] SURGICAL KNOT PUSHER WITH FLATTENED SPATULATED TIP

[76] Inventor: Robert W. Mericle, 103 Morgan Rd., Eden, N.C. 27288

[21] Appl. No.: 633,076

[22] Filed: Apr. 16, 1996

[51] Int. Cl.⁶ ................................................. A61B 17/04
[52] U.S. Cl. ............................ 606/148; 606/144; 606/148
[58] Field of Search ................................ 606/139, 144, 606/148

[56] References Cited

U.S. PATENT DOCUMENTS

| | | | |
|---|---|---|---|
| 5,391,175 | 2/1995 | Sharpe et al. | 606/148 |
| 5,395,382 | 3/1995 | DiGiovanni et al. | 606/148 |
| 5,397,326 | 3/1995 | Mangum | 606/148 |
| 5,403,330 | 4/1995 | Tuason | 606/148 |
| 5,423,837 | 6/1995 | Mericle et al. | 606/148 |
| 5,601,576 | 2/1997 | Garrison | 606/148 |
| 5,628,758 | 5/1997 | Otten et al. | 606/148 |

*Primary Examiner*—Michael Buiz
*Assistant Examiner*—T. D. Pham
*Attorney, Agent, or Firm*—Gipple & Hale; John S. Hale

[57] ABSTRACT

A surgical knot pusher for pushing a suture knot along a suture strand, comprising an elongated tube with a flattened tip formed on the distal end of the elongated tube. The flattened tip is provided with opposing resilient jaws defining a slot therebetween which leads to an eyelet defined by the flattened tip for containing an advancing length of the suture while the suture knot is being pushed allowing the suture strand to easily enter the eyelet while preventing the suture strand from exiting the eyelet. A cutting assembly is slidably mounted within the elongated tube and comprises a rod with a blade having a straight linear edge mounted on one end and a handle on the other end. The blade is biased away from the flattened tip by a spring mounted on the rod, the spring engaging the flattened tip when the blade is moved toward the eyelet by pushing the handle toward the tip.

10 Claims, 6 Drawing Sheets

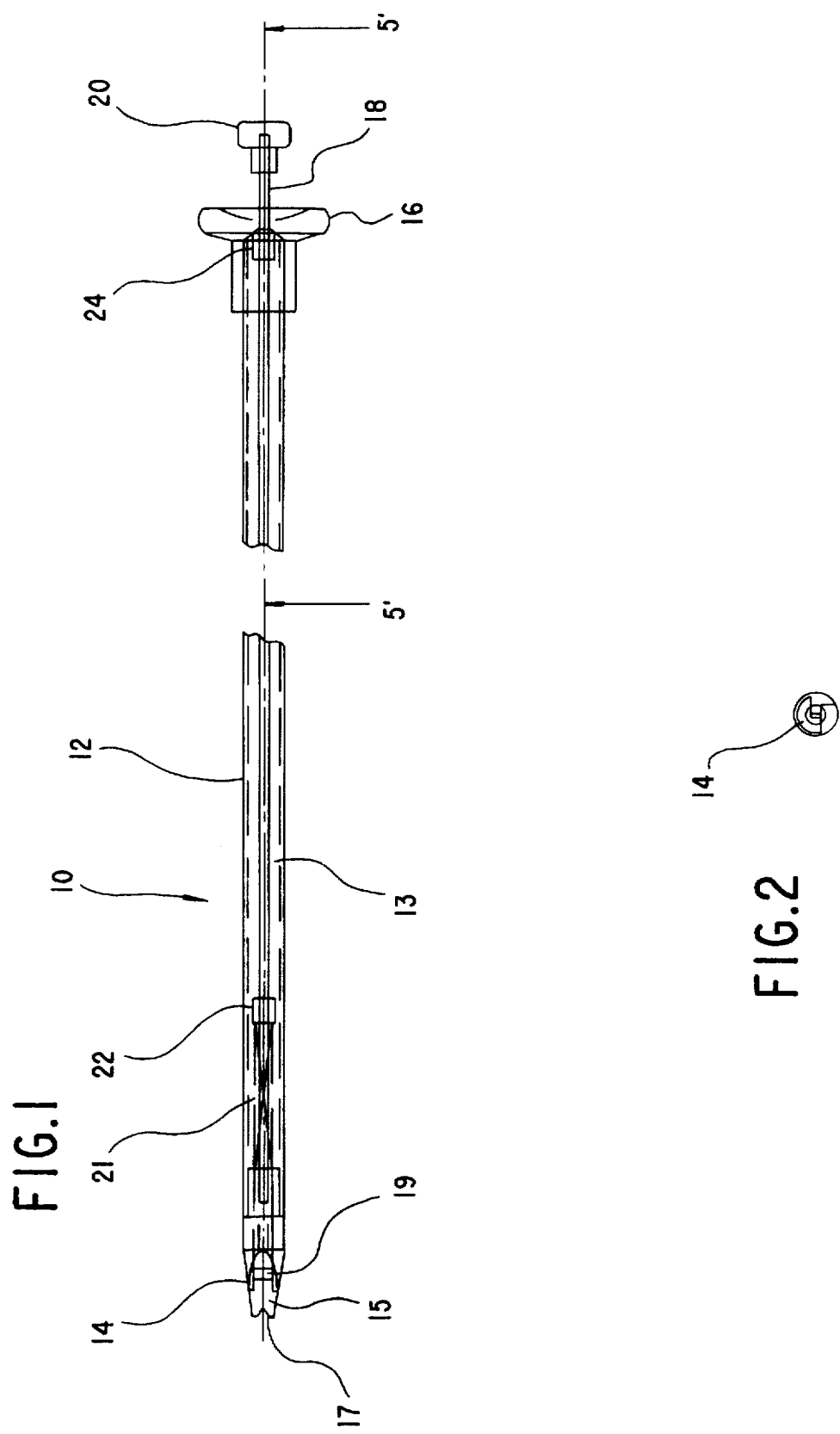

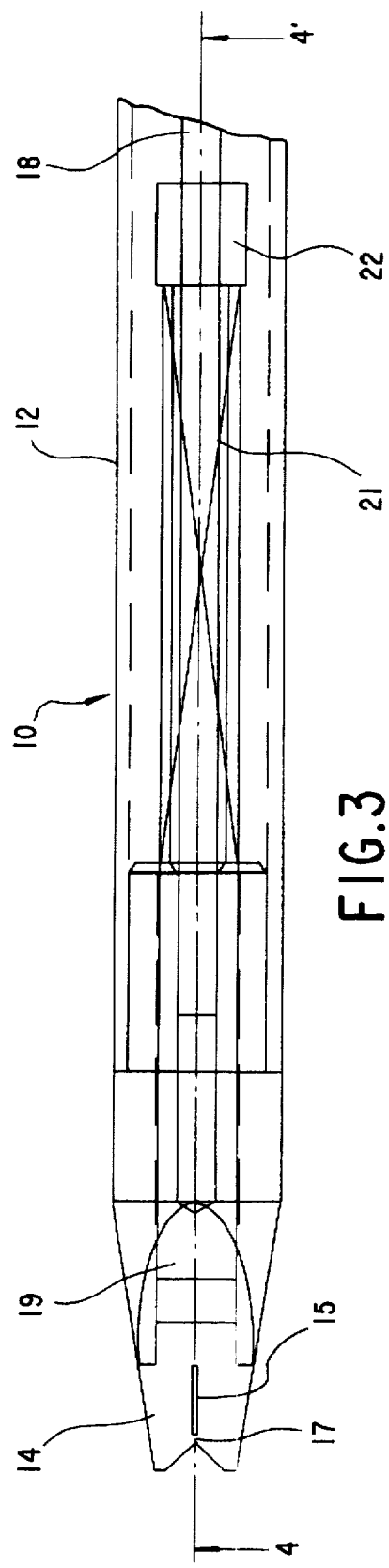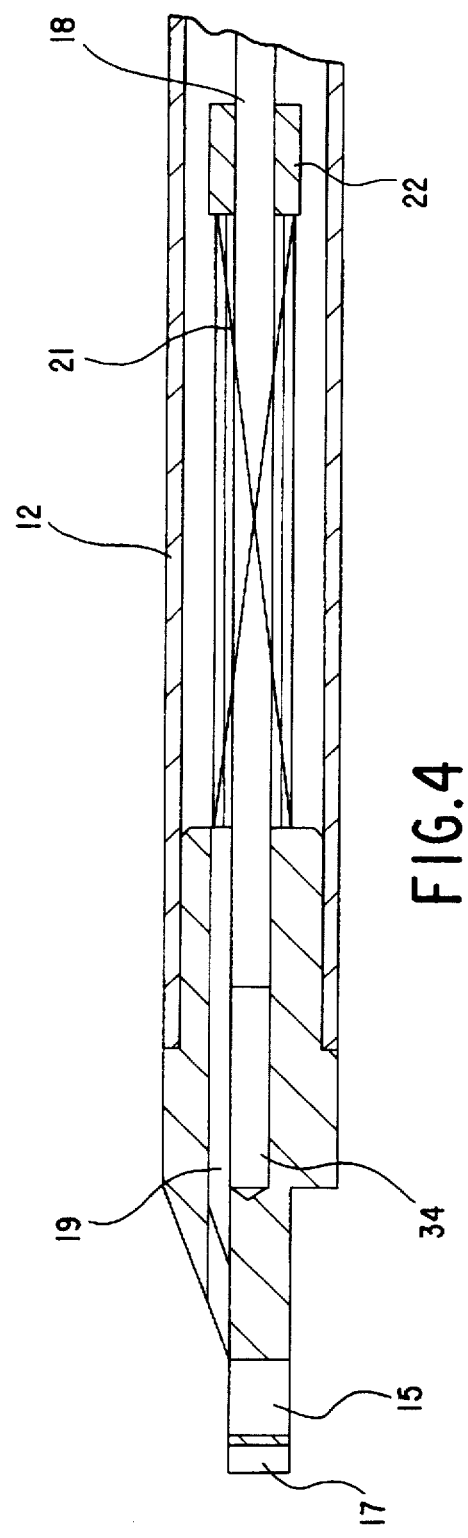

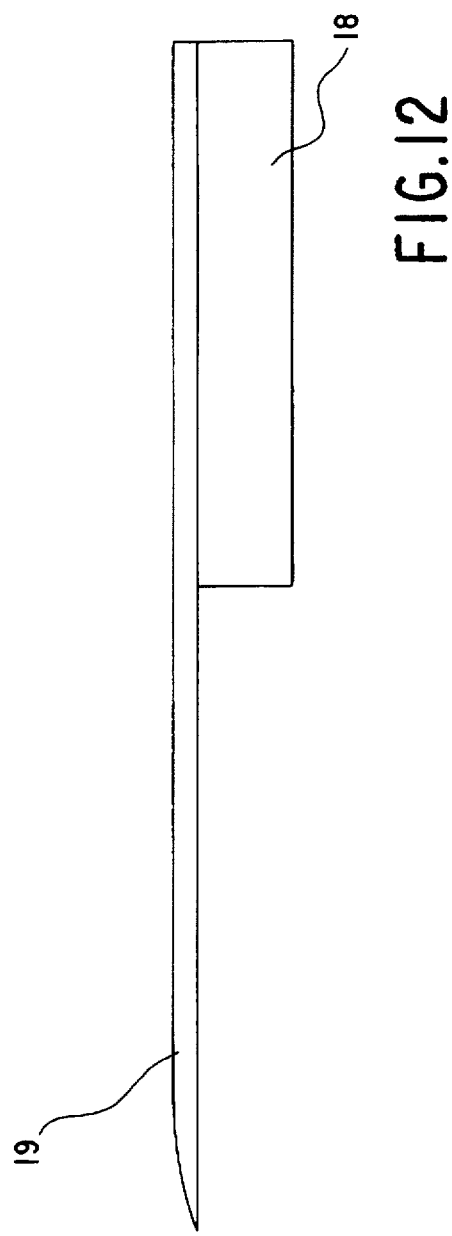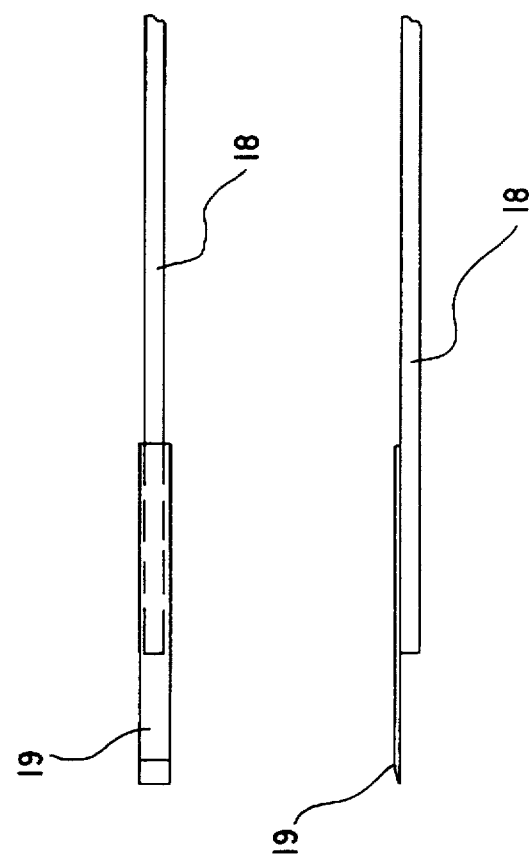

SURGICAL KNOT PUSHER WITH FLATTENED SPATULATED TIP

BACKGROUND OF THE INVENTION

1. Field of the Invention

The present invention relates generally to surgical knot tying and cutting tools, and relates more particularly to a suturing and ligation tool used during an endoscopic surgical procedure.

The invention is specifically directed toward a surgical knot pusher designed to push suture knots which have been tied extracorporeally or outside of the body during a surgical procedure toward the tissue to be approximated and then to cut the suture strands once the knot has been tied in the proper position.

2. Description of the Prior Art

The use of knot pushers in surgical procedures to assist with placement of extracorporeally tied knots to close severed blood vessels and other small fluid ducts is well known in the art. A number of prior art patents have been directed toward such surgical knot pushers.

One such U.S. Pat. No. 5,423,837 issued Jun. 13, 1995 to the present inventor shows a surgical knot pusher with a truncated conical tip forming an endwall with a guide opening to accommodate a suture. The suture enters the opening through a slit and the slit opens into a complex configured suture slot which is cut into the side of the conical tip. This knot pusher uses a rigid tube to cut the suture which does not cut the suture effectively.

Another U.S. Pat. No. 5,269,791 issued Dec. 14, 1993 discloses a surgical knot pusher having a tapered spiral coil on the tip, with the respective coils being spaced to receive a suture. The conically tapered coil narrows to an opening at the end that is slightly larger than the diameter of the suture but is small enough to prevent the suture from slipping off the surgical knot pusher. This surgical knot pusher is not provided with a cutter.

U.S. Pat. No. 5,176,691 issued Jan. 5, 1993 shows a surgical knot pusher having an opposed pulley-like surface for guiding the ends of the suture away from the winding of a knot as the winding is advanced through the portal of an endoscope. This surgical knot pusher does not use a cutter.

U.S. Pat. No. 5,084,058 issued Jan. 28, 1992 discloses a suture rundown tool and cutter assembly. The knot rundown tool is in the form of an elongated shaft with a convex, V-shaped groove formed in the front end of the shaft. The shaft includes a pair of diametrically-opposed elongated grooves which intersect the base of the V-shaped groove and extend rearwardly therefrom and a pair of diametrically opposed, V-shaped notches formed in the front ends of the elongated grooves of the shaft.

U.S. Pat. No. 4,961,741 issued Oct. 9, 1990 shows a suture knotting instrument for forming a double knot. The device consists of two parts, a leading member and a trailing member, with the leading member being designed to slide a first knot against the tissue and the trailing member being designed to slide a second knot against the first knot. The leading member is designed to part as the trailing member slides the second knot against the first.

U.S. Pat. No. 4,641,652 issued Feb. 10, 1987 is directed toward an applicator for tying sewing threads used in combination with an endoscope tube. The applicator is a hollow coil communicating with a longitudinal passage through a shaft. This device does not provide a cutter.

Another U.S. Pat. No. 4,602,635 issued Jul. 29, 1986 is directed toward a remote surgical knot tier and method of use. The knot tier can be inserted down a hollow cannula inserted in the skin around the knee joint. The device uses a cylindrical rod member having an angularly cast end which may be non-perpendicular to the length of the rod member. The rod member has a flat face at the end with a small hole therein to accommodate the passage of a suture therethrough. This device does not provide a cutter.

Still another U.S. Pat. No. 3,752,516 issued Aug. 14, 1973 discloses a knot tying jig formed of a hollow cylindrical tube having one or both of its ends cut at about forty degrees to provide slanted ends. The slanted end or ends are provided with notches on the center line of the tube and extend transversely across the slanted ends. A hole is provided in each end of the tube to accommodate the suture. The jig is not provided with a cutter.

Surgical knot placement is frequently a difficult task when access to the wound site is impeded because bodily fluids make the suturing material difficult to hold and tie. This is particularly true in laproscopic surgery procedures, where the surgeon is normally attempting to tie a surgical knot using instruments which can only access the wound area through the small access ports used during such procedures. In such cases a surgical knot pusher may be employed to tighten the suture knot. The surgical knot is first tied loosely, and then advanced down the loop of suture by the pusher, resulting in a tight closure at the wound site.

Once the suture needle passes outside of the access port the surgeon can tie a surgical slip knot outside of the body or "extracorporeally". Having done this, the knot pusher can be used to advance the knot toward the tissue through the access port, while firmly holding the free end of the suture outside the body. The knot will tighten at the tissue surface and lock in position. This approach to knot tying, especially in laproscopic surgery procedures, can significantly benefit the patent and surgeon alike, reducing the time needed to complete the surgical procedure.

Various knot pushers are available and examples of these have been previously discussed.

Many prior art devices either require the suture to be threaded through a small hole or held within the crotch of a fork. Threading a suture through a small hole is difficult to do during an operating procedure and is sensitive to the size of the suture. When the suture is to be held within the crotch of a fork there is a tendency for the suture to fall out of the V-shaped area. None of these devices offers the surgeon a means for cutting the excess suture material from the knot after successfully placing it adjacent to the desired area. The present invention not only places the knot, but has its own cutting feature which eliminates the need for another instrument such as scissors to accomplish this function.

SUMMARY OF THE INVENTION

The surgical knot pusher device is constructed with an elongated shaft having a flattened spatulated tip which is slotted and provided with an eyelet which restricts the suture and prevents it from falling out of the flattened spatulated tip. The suture is easily positioned without threading by pushing the slot on the tip against the suture forcing the suture through the slot and into the eyelet.

A cutting device is incorporated into the surgical knot pusher, by providing the inside of the elongated shaft with a movable rod member which has a cutting blade affixed to the distal end. The surgeon advances the cutting blade toward the suture by pushing on an actuator knob mounted on the distal end of the rod member as the knob protrudes from the end of the elongated shaft. A tensioning spring is provided within the shaft to maintain the blade in a retracted position until it is used to sever the suture. When the cutting blade is advanced toward the suture, it advances against a counter force provided by the tensioning spring or similar device. When the suture is cut, the surgeon ceases applying pressure to the rod and the cutting blade retracts to its original position due to the force applied by the spring.

It is therefore an object of the present invention to provide a surgical knot pusher which offers the surgeon simplicity of use.

Another object of the invention is to provide a surgical knot pusher which will reliably advance the surgical knot without the suture material slipping out of the device.

Another object of the invention is to provide a surgical knot pushing tool which can precisely cut the excess suture material from the tied knot.

Another object of the invention is to provide a surgical knot pusher which is easily and inexpensively manufactured.

In the accompanying drawings, there is shown an illustrative embodiment of the invention from which these and other objectives, novel features and advantages will be readily apparent.

BRIEF DESCRIPTION OF THE DRAWINGS

FIG. 1 is a side view of the inventive knot pusher device shown with a missing central portion to illustrate indeterminate length;

FIG. 2 is an end elevational view of the tip of the knot pusher device shown in FIG. 1;

FIG. 3 is an enlarged view of the end of the knot pusher device shown in FIG. 1;

FIG. 4 is a cross sectional view of the device shown in FIG. 3 taken along the line 4'—4';

FIG. 10 is a plan view of the cutting assembly used with the surgical knot pusher;

FIG. 11 is a side view of the cutting assembly shown in FIG. 10;

FIG. 12 is an enlargement of the encircled portion of FIG. 11; and

DETAILED DESCRIPTION OF THE PREFERRED EMBODIMENT

Figure 5:
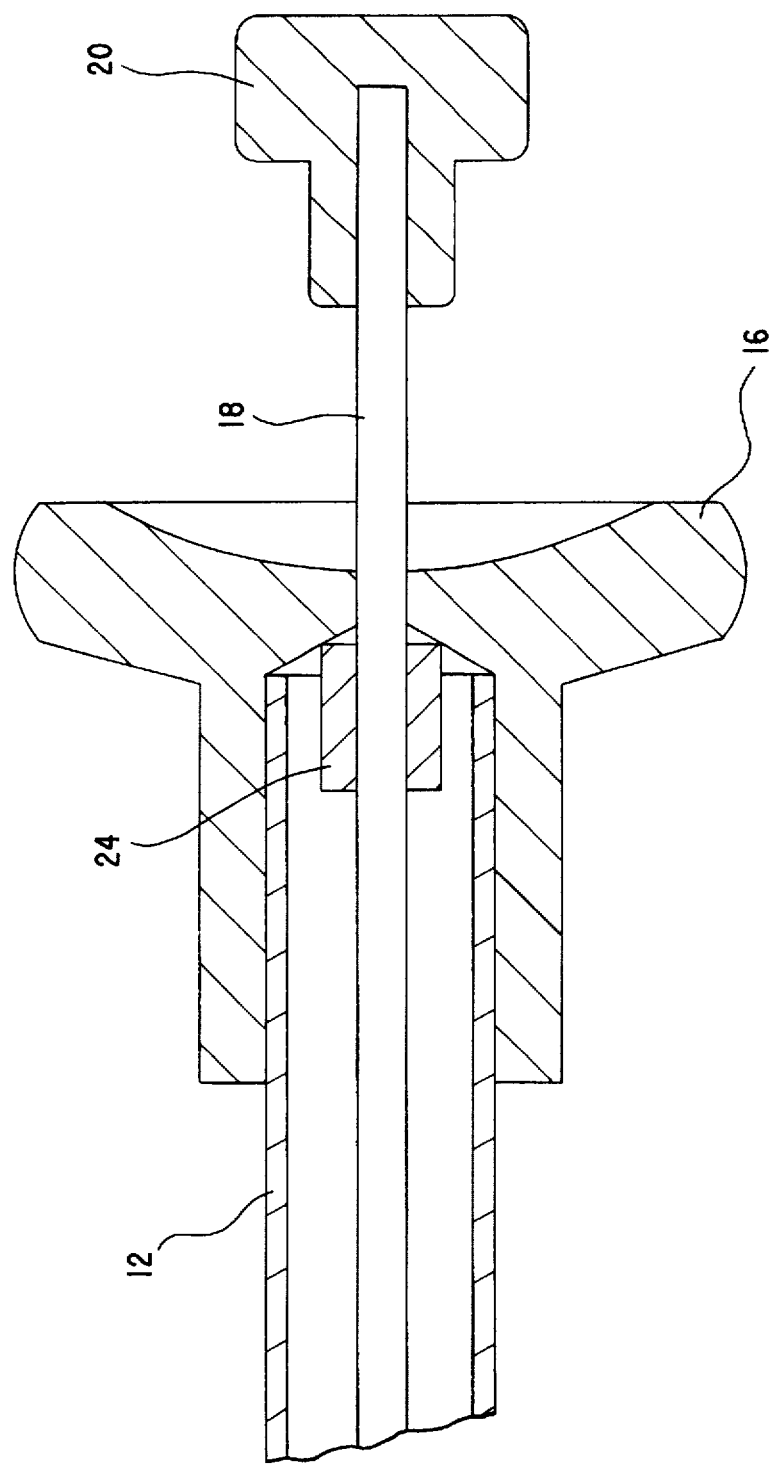
FIG. 5 is an enlarged cross sectional view of a cut away portion taken along the line 5'—5' of FIG. 1.

The invention is now described with reference to an exemplary embodiment shown in the drawings. The preferred embodiment and best mode of the invention is shown in FIGS. 1-13.

The surgical knot pusher 10 includes an elongated shaft or tube 12 defining a thoroughgoing bore 13, the shaft having a flattened spatulated tip 14 on one end defining an eyelet 15 and entrance slot 17 and a handle 16 mounted at the other end. A cutting assembly is mounted in the elongated shaft and is formed by an actuation rod 18 disposed within the elongated shaft 12 extending from the elongated shaft 12 at one end. Actuation knob 20 is connected to one end of the actuation rod 18 and a cutting blade 19 is mounted to the other or distal end of the actuation rod 18. The actuation rod 18 is slidably mounted within elongated shaft 12. A rear stop 24 is positioned at the proximal end of the actuation rod 18 and is secured thereto to limit withdrawal of rod 18 from shaft 12. A tensioning spring 21 surrounds the lower portion of actuation rod 18 and is secured to spring anchor 22. Spring anchor 22 and tensioning spring 21 thereby cooperate to exert a biasing force on the actuation rod 18 which is directed longitudinally along the actuation rod 18 toward the actuation knob 20 when the actuation knob is pushed forward. When the surgeon releases the actuation knob 20 after severing the sutures, the force from the tensioning spring 21 slides the actuation rod 18 and the cutting blade 19 back into a resting position away from the eyelet 15 to the position shown in FIG. 4. Thus the actuation rod 18 and cutting blade 19 are in the resting position so that there is a reduced risk of inadvertently cutting the suture material. This resting position allows the loading of the suture for another knot pushing operation. The spring return pressure is controlled by changing the position of the spring anchor 22 on the rod 18.

FIGS. 3 and 4 show an enlarged top view of the end of the elongated shaft 12 of the surgical knot pusher 10 showing the tensioning spring 21 and the flattened spatulated tip 14 in greater detail. The actuation rod 18 and cutting blade 19 are in a retracted position with no tension on the tensioning spring 21.

The lower portion of the handle 16 is mounted on the end of the elongated shaft 12. Actuation rod 18 passes through the handle 16 as it enters elongated shaft 12. The rear stop 24 prevents actuation rod 18 from being removed from elongated shaft 12.

Figure 6:
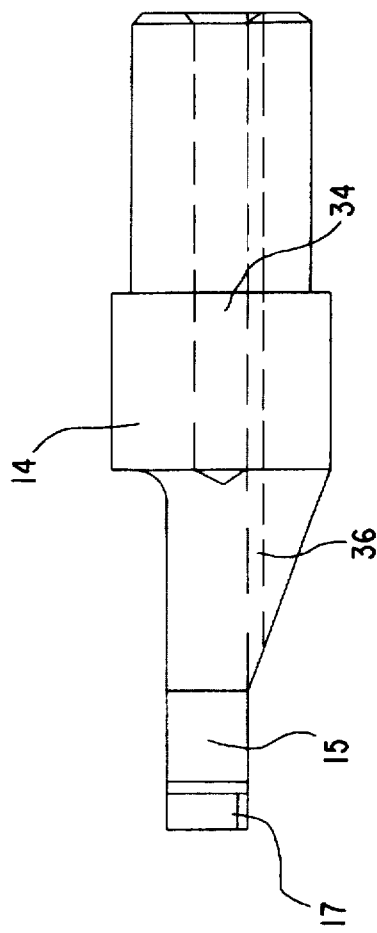
FIG. 6 is an enlarged side view of a schematic representation of one embodiment of the flattened spatulated tip.
Figure 7:
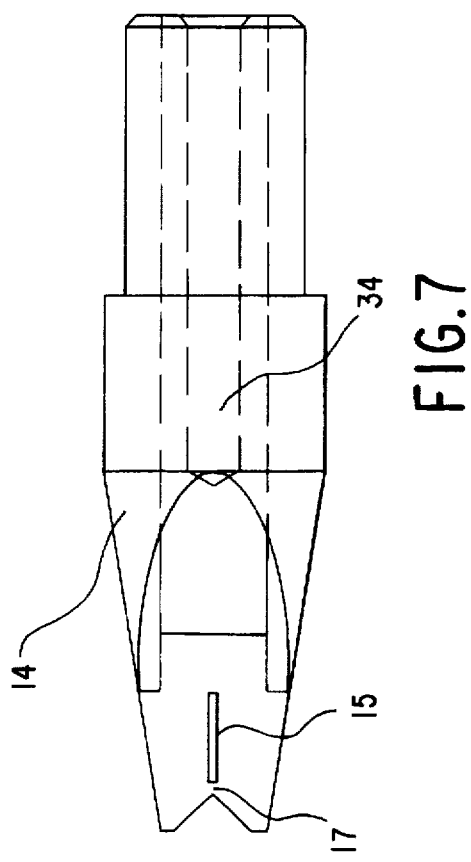
FIG. 7 is an enlarged plan view of the flattened spatulated tip of FIG. 6.

An actuation rod groove 34 as shown in FIGS. 6 and 7 is cut in to the tip 14. The actuation rod groove 34 provides a travel path for the actuation rod 18 as the actuation knob 20 is pressed toward the handle 16 by the surgeon. The actuation rod 18 moves forward in the groove 34 until it reaches the end of its travel path, the forward travel being limited by the actuation rod 18 engaging the end of the actuation rod groove 34. A cutting blade groove or track 36 is also shown in dotted line outline. As the actuation rod 18 and cutting blade 19 move toward the eyelet 15, the cutting blade 19 travels in the cutting blade groove 36.

Figure 9:
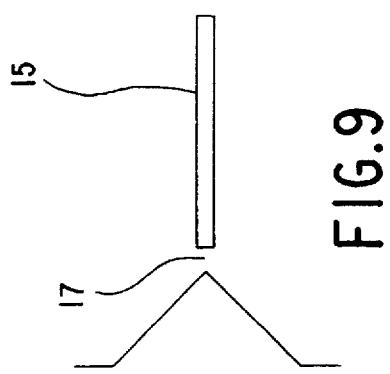
FIG. 9 is an enlarged partial plan view of the flattened spatulated tip shown in FIG. 7.
Figure 8:
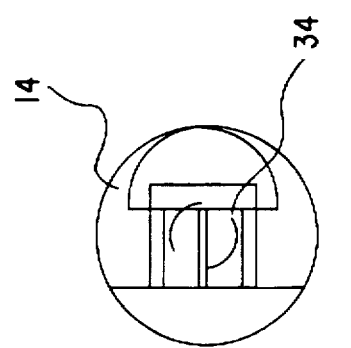
FIG. 8 is a front end view of the flattened spatulated tip shown in FIG. 7.

The relative positioning and approximate dimensions of the eyelet 15, the tip slot 17 and tip notch 39 on the flattened spatulated tip 4 are illustrated in FIGS. 7 and 9.

Figure 13:
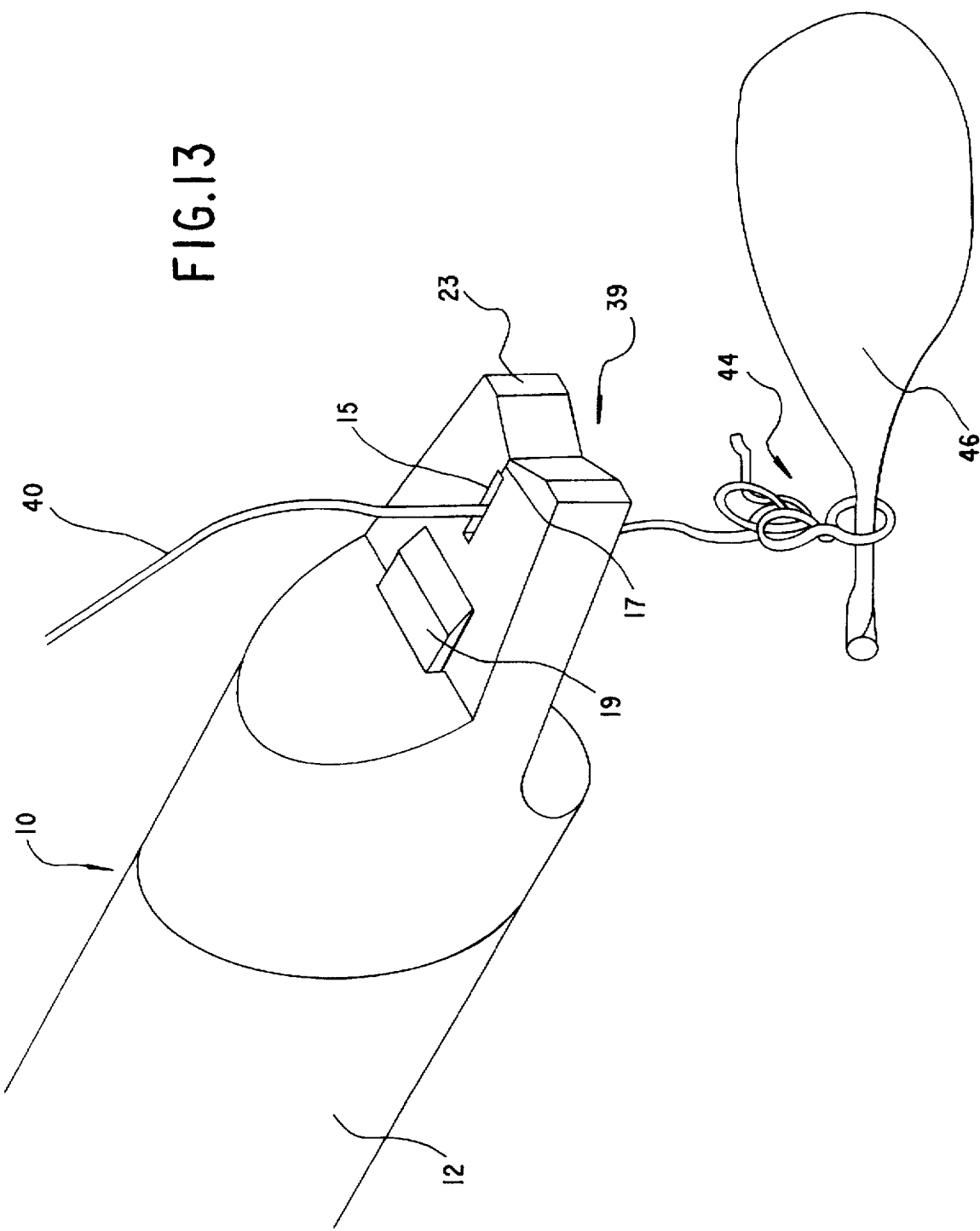
FIG. 13 is a perspective view of one end of the surgical knot pusher showing the suture in place in the surgical knot pusher and a surgical slip knot in place around a blood vessel to be sutured.

A surgical knot pusher showing the suture in place in the surgical knot pusher and a surgical slip knot in place around a vessel to be tied shut is shown in FIG. 13. The term "suture" as used in this application includes ligature and filamentary material which may be used in a surgical procedure. The cutting blade 19 is shown in its retracted position in the surgical knot pusher 10 with the suture 40 shown in position in the eyelet 15. When the knot 44 is tightened around the vessel protruding from the body member 46, the suture 40 can be severed by the cutting blade 19. During the cutting procedure the suture is slipped into the eyelet 15 of the flattened spatulated tip 14 directly behind the knot 44. The knot 44 is snugged against the side of the flattened spatulated tip 14 opposite the cutting blade 19 and advanced to the body member 46. The thickness of the spatulated tip 14 determines the precise length of the cut suture tail. The tip thickness can be altered to idealize this cut length. After snugging the knot 44, the cutting blade 19 is advanced along the tip surface and severs the suture in a slicing manner. If desired, the angle of the cutting blade 19 may be altered so that the cutting blade 19 engages the suture 40 with a angular slicing motion for improved effectiveness cutting the suture.

The flattened spatulated tip 14 is preferably made from a resilient material which allows the jaws 23 defining the tip slot 17 in the flattened spatulated tip 14 to resiliently expand to permit suture materials of various diameters to enter the eyelet 15. Once the suture 40 is positioned in the eyelet 15, the jaws 23 of the flattened spatulated tip 14 return to normal shape ensuring that the suture 40 will not come out of the eyelet 15 while the surgical knot 44 is being pushed. Thus the flattened spatulated tip 14 should exhibit sufficient flexibility and resiliency to allow a range of suture materials to enter the eyelet 15 through the tip slot 17 without easily becoming dislodged from the eyelet 15. Sufficiently springy materials which can be used for the tip construction can be non-metallic materials such as polymers or suitable composite materials. Superelastic nickel-titanium alloys, hard polyurethanes, nylons, polycarbonates, polyetheretherketones, ultrahigh molecular weight polyethylene can also be used. However, the flattened spatulated tip 14 may be made of any material and may constitute a disposable and replaceable part of the device.

The elongated shaft 12 preferably comprises a tube of relatively stiff material in order to avoid undesirable flexing. Appropriate materials, such as stainless steel and aluminum, engineered polymer materials such as polyetheretherketones, polyphenylene oxide, polyphenylene sulfide and polymer composite such as glass-filled epoxy resin, carbon fiber-filled epoxy resin, and other suitable natural or synthetic resin materials can be used.

The cutting blade 19 preferably is constructed with a straight blade that is beveled on one side and is secured to the actuation rod 18 by adhesives, sonic welding or other means known in the art. The cutting blade 19 can have other shapes, however, and the actuation rod 18 and cutting blade 19 can be manufactured as a single piece from a single piece of material such as stainless steel or as separate pieces which are then affixed to one another as previously noted.

In normal operation of the surgical knot pusher 10, a surgeon will have sewn a loop of suture material across an incision in a patient. The two loose ends of the suture material will extend outside the body of the patient so that a surgical slip knot 44 in one end of the suture material can be loosely tied around the other loose end of the suture material. The loose end of the suture at a position above the knot is aligned with the tip notch 39 and the flattened spatulated tip 14 is moved toward the suture, forcing the suture into and through the tip slot 17 and then into the eyelet 15. The surgical knot 44 is located at the opposite side of the tip 14 from the cutting blade 19. The surgical knot 44 is then pushed with the flattened spatulated tip 14 along the suture strand 40 toward the incision to be approximated. The slack in the loose end is taken up by the surgeon pulling the loose end of the suture 40 through the eyelet 15 as the knot 44 is being pushed. The surgical knot 44 is pushed until the suture is tightly closed. The remaining suture material can be severed by depressing the actuation knob 20 which will move the cutting blade 19 across the eyelet 15, cutting the suture strand. The thickness of the spatulated tip is designed to provide suture cutting at a precise distance from the knot.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. A surgical knot pusher for pushing a suture knot along a suture strand, comprising:

an elongated shaft;

a flattened spatulated tip with resilient jaws secured to the distal end of the elongated shaft;

suture holding means disposed on said flattened spatulated tip for containing an advancing length of the suture while the suture knot is being pushed; and entry means on said flattened spatulated tip for said suture strand, said entry means comprising said opposing resilient jaws defining a suture passageway therebetween allowing the suture to easily enter the suture holding means which is an enclosed eyelet, while preventing the suture from exiting said suture holding means, said entry means comprising said suture passageway running from the distal end of the flattened spatulated tip to said enclosed eyelet defined by said spatulated tip, the suture passageway providing a means for the suture to enter said enclosed eyelet and having a width less than the diameter of the suture, said distal end of the flattened spatulated tip is provided with a tip notch leading into said suture passageway, the tip notch being substantially V shaped with the vertex of the V coinciding with the distal end of the suture passageway to guide the suture into the suture passageway.

2. A surgical knot pusher as claimed in claim 1 further comprising cutting means slidably mounted in said elongated shaft for cutting the suture strand as it emerges from said eyelet defined by said flattened spatulated tip; said cutting means comprising a rod with a blade having a straight linear edge mounted in said shaft and biased away from said flattened spatulated tip by spring means.

3. A surgical knot pusher for pushing a suture knot along a suture strand, comprising:

an elongated shaft;

a flattened spatulated tip secured to the distal end of the elongated shaft;

suture holding means formed on said flattened spatulated tip for containing an advancing length of the suture while the suture knot is being pushed;

entry means defined on said flattened spatulated tip for engaging suture strand, said entry means allowing the suture strand to easily enter the suture holding means, but preventing the suture strand from exiting said suture holding means; a cutting means slidably disposed within said elongated shaft, said flattened spatulated tip being provided with a cutting means channel which allows the cutting means to move out of the flattened spatulated tip toward the suture strand; and cutter moving means disposed within said elongated shaft for moving the cutting means through the cutting means channel toward the suture strand emerging from the suture holding means; said cutting means comprising a flat, straight-edged blade and said cutter moving means is an actuation rod slidably disposed within said elongated shaft, said straight-edged blade being affixed to the distal end of the actuation rod and the proximal end of said actuation rod extending from the proximal end of the elongated shaft wherein the angle of the straight-edged blade relative to the straight-edged direction of the travel of the blade being changeable so that the straight-edged blade can slice the suture strand at a desired angle.

4. A surgical knot pusher as claimed in claim 3 further comprising biasing means secured to said actuation rod for biasing said straight-edged blade and said actuation rod toward the proximal end of said elongated shaft, said biasing means comprising a tensioning spring positioned adjacent to said actuation rod and secured to a collar mounted to said actuation rod moving said straight-edged blade away from the suture holding means when the straight-edged blade is not in use.

5. A surgical knot pusher as claimed in claim 4 further comprising spring tension adjusting means for adjusting the magnitude of the force exerted by the tensioning spring on the actuation rod and said straight-edge blade to move said straight-edged blade away from the suture holding means when the straight-edge blade is not in use.

6. A surgical knot pusher as claimed in claim 3 wherein a surface of the flattened spatulated tip from the cutting channel to the suture holding means is planar.

7. A surgical knot pusher for pushing a suture knot along a suture strand, comprising:

an elongated tube;

a flattened head formed on the distal end of the elongated tube to provide visibility of the suture strand during cutting, said flattened head being provided with opposing resilient jaws defining a slot therebetween; said slot leading to an enclosed eyelet defined by said head for containing an advancing length of the suture while the suture knot is being pushed allowing the suture strand to easily enter the eyelet while preventing the suture strand from exiting the eyelet;

a cutting assembly slidably mounted within said elongated tube, said cutting assembly comprising a rod with a straight edged blade mounted on one end and a handle on the other end; said straight edged blade being biased away from said flattened head by spring means mounted on said rod, said spring means engaging said flattened head when the straight-edged blade is moved toward the eyelet by pushing the handle toward the head.

8. A surgical knot pusher as claimed in claim 7 wherein the distal end of the flattened head defines a head notch with a substantially V shaped configuration, the vertex of the V coinciding with the distal end of the head slot to guide the suture into the head slot.

9. A surgical knot pusher as claimed in claim 7 wherein said spring means comprises a spring holder mounted on said rod, a spring mounted to said spring holder and extending from said spring holder toward said head to bias said rod against the force applied to said handle when the straight-edged blade is pushed toward the eyelet and transporting said rod away from said eyelet when the force on the handle is removed.

10. A surgical knot pusher as claimed in claim 7 including limiting means mounted on said rod to limit movement of the rod when forced forward by said handle.

* * * * *